US012268541B2

(12) United States Patent
Ogawa et al.

(10) Patent No.: US 12,268,541 B2
(45) Date of Patent: Apr. 8, 2025

(54) MAMMOGRAPHY APPARATUS

(71) Applicant: FUJIFILM Corporation, Tokyo (JP)

(72) Inventors: Daisuke Ogawa, Kanagawa (JP);
Kohei Ota, Kanagawa (JP); Takeyasu Kobayashi, Kanagawa (JP); Sayaka Saito, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 80 days.

(21) Appl. No.: 18/457,310

(22) Filed: Aug. 28, 2023

(65) Prior Publication Data
US 2024/0065658 A1 Feb. 29, 2024

(30) Foreign Application Priority Data

Aug. 30, 2022 (JP) .................. 2022-137271

(51) Int. Cl.
*A61B 6/50* (2024.01)
*A61B 6/00* (2024.01)
A61B 6/04 (2006.01)

(52) U.S. Cl.
CPC ............ *A61B 6/4488* (2013.01); *A61B 6/502* (2013.01); *A61B 6/0414* (2013.01)

(58) Field of Classification Search
CPC ..... A61B 6/502; A61B 6/4488; A61B 6/0492; A61B 6/08; A61B 2090/366
See application file for complete search history.

(56) References Cited

U.S. PATENT DOCUMENTS

| 2009/0080605 A1* | 3/2009 | Miyako | ................ | A61B 6/0414 250/370.15 |
| 2009/0080606 A1* | 3/2009 | Ohta | .................... | A61B 6/4488 378/37 |
| 2009/0080620 A1* | 3/2009 | Miyako | .................. | A61B 6/502 378/199 |

(Continued)

FOREIGN PATENT DOCUMENTS

| JP | 2007236805 A | 9/2007 |
| KR | 10-2014-0136585 A | 12/2014 |

OTHER PUBLICATIONS

The extended European search report issued by the European Patent Office on Jan. 11, 2024, which corresponds to European Patent Application No. 23193966.1-1126 and is related to U.S. Appl. No. 18/457,310.

*Primary Examiner* — Colin T. Sakamoto
(74) *Attorney, Agent, or Firm* — Studebaker Brackett PLLC

(57) ABSTRACT

A mammography apparatus includes: an arm; a first cooling fan that is disposed on a stand side with respect to the radiation source in the arm, sucks air from an outside of the arm, and discharges air that has cooled the radiation source from a first exhaust port provided on the stand side with respect to the radiation source; a projector that is disposed in the arm; a second cooling fan that is disposed between the projector and the first exhaust port in the arm, sucks a part of air directed from the first cooling fan to the first exhaust port, blows the sucked air toward the projector to cool the projector, and has a flow rate smaller than that of the first cooling fan; and a second exhaust port that is provided separately from the first exhaust port and through which air that has cooled the projector is discharged.

6 Claims, 6 Drawing Sheets

(56) References Cited

U.S. PATENT DOCUMENTS

| | | | |
|---|---|---|---|
| 2014/0341336 A1* | 11/2014 | Kim | A61B 6/502 |
| | | | 378/37 |
| 2021/0401381 A1* | 12/2021 | Wells | A61B 6/08 |
| 2022/0047229 A1* | 2/2022 | Takata | A61B 6/0414 |
| 2024/0038480 A1* | 2/2024 | Freudenberger | A61B 6/03 |

* cited by examiner

MAMMOGRAPHY APPARATUS

CROSS-REFERENCE TO RELATED APPLICATION

This application claims priority from Japanese Patent Application No. 2022-137271, filed Aug. 30, 2022, the disclosure of which is incorporated herein by reference in its entirety.

BACKGROUND

Technical Field

The present disclosure relates to a mammography apparatus.

Related Art

JP2007-236805A discloses an X-ray diagnostic apparatus for mammography comprising: X-ray exposure means for exposing X-rays (for example, corresponding to a radiation source), an X-ray plane detector for detecting X-rays incident on a detection surface, a compression plate for compressing and fixing a breast, and projection means for projection a reference image which is referred to in a case of fixing the breast by the compression plate onto the compression plate or the detection surface. The technology described in JP2007-236805A discloses that the projection means (for example, a projector) is used to project the reference image (for example, a skin line) for positioning the breast onto the compression plate or the detection surface. The projection means is provided in an arm accommodating an X-ray tube.

In the mammography apparatus, for example, a cooling fan is provided in an arm accommodating a radiation source. The cooling fan cools the radiation source with air sucked from the outside and discharges the air that has passed through the radiation source to the outside through an exhaust port. In such a mammography apparatus, a method of cooling a projector accommodated in the arm has been studied. For example, a cooling method is conceivable in which the projector is cooled by the air sucked from the outside in the same manner as the radiation source, and the air that has passed through the projector is discharged to the outside through the same exhaust port.

However, in this cooling method, a cooling efficiency of the projector may be decreased. This is because a size of the radiation source is larger than that of the projector, so that a flow rate of the air passing through the radiation source needs to be larger than that of the projector. Therefore, in a case where the air directed from the radiation source to the exhaust port and the air directed from the projector to the exhaust port are merged in front of the exhaust port and then discharged from the exhaust port, a flow of the air cooling the projector is obstructed and the cooling efficiency of the projector may be decreased.

JP2007-236805A does not describe a configuration for cooling the radiation source and the projector.

SUMMARY

The technology of the present disclosure provides a mammography apparatus capable of efficiently cooling a projector.

A first aspect of the technology of the present disclosure is a mammography apparatus comprising: an arm that accommodates a radiation source emitting radiation toward a breast and is supported by a stand; a first cooling fan that is disposed on a stand side with respect to the radiation source in the arm, sucks air from an outside of the arm, and discharges air that has cooled the radiation source from a first exhaust port provided on the stand side with respect to the radiation source; a projector that is disposed in the arm and projects information; a second cooling fan that is disposed between the projector and the first exhaust port in the arm, sucks a part of air directed from the first cooling fan to the first exhaust port, blows the sucked air toward the projector to cool the projector, and has a flow rate smaller than that of the first cooling fan; and a second exhaust port that is provided separately from the first exhaust port and through which air that has cooled the projector is discharged.

A second aspect of the technology of the present disclosure is the mammography apparatus according to the first aspect, further comprising: a first flow path in which the first cooling fan is disposed and that is directed from the first cooling fan to the first exhaust port; and a second flow path that is directed from a branch portion branching from the first flow path to the second exhaust port between the first cooling fan and the first exhaust port and in which the second cooling fan and the projector are disposed, in which a partition is provided between the first flow path and the second flow path except for the branch portion.

A third aspect of the technology of the present disclosure is the mammography apparatus according to the second aspect, in which a first distance from an end surface of the radiation source on a first cooling fan side to the second cooling fan via the branch portion is longer than a second distance from the end surface to the first exhaust port.

A fourth aspect according to the technology of the present disclosure is the mammography apparatus according to the first aspect, in which a light source of the projector is disposed on a second cooling fan side with respect to the second exhaust port.

A fifth aspect according to the technology of the present disclosure is the mammography apparatus according to the first aspect, in which an emission port through which projection light is emitted from the projector also serves as the second exhaust port.

A sixth aspect according to the technology of the present disclosure is the mammography apparatus according to the second aspect, in which the projector is disposed on a radiation source side with respect to the first cooling fan and the second cooling fan, and in a case where the first flow path and the second flow path are viewed as a whole, the first flow path and the second flow path form a V-shape with the branch portion as an apex.

The technology of the present disclosure can provide a mammography apparatus capable of efficiently cooling the projector.

DETAILED DESCRIPTION

Hereinafter, an embodiment of the present disclosure will be described in detail with reference to the drawings.

In the following description, for convenience of explanation, a height direction, a width direction, and a front-rear direction (also referred to as a depth direction) of the mammography apparatus 10 are indicated by three arrows X, Y, and Z. First, the height direction is indicated by the arrow Z, an arrow Z direction pointed by the arrow Z is an upward direction of the mammography apparatus 10, and an opposite direction of the upward direction is a downward direction. The height direction is a vertical direction. The width direction is indicated by the arrow X orthogonal to the arrow Z, a direction pointed by the arrow X is a right direction of the mammography apparatus 10, and an opposite direction of the right direction is a left direction. The front-rear direction is indicated by the arrow Y orthogonal to the arrow Z and the arrow X, a direction pointed by the arrow Y is a front direction of the mammography apparatus 10, and an opposite direction of the front direction is a rear direction. That is, in the mammography apparatus 10, a stand 20 side is the rear direction, and an opposite side thereof on which a subject A stands (see FIG. 2) is the front direction. In addition, in the following, expressions using sides such as an upper side, a lower side, a left side, a right side, a front side, and a rear side have the same meanings as the expressions using the directions.

In the present embodiment, a "vertical direction" refers not only to a perfect vertical direction but also to a vertical direction in the sense of including an error that is generally acceptable in the technical field to which the technology of the present disclosure belongs and that does not contradict the concept of the technology of the present disclosure. The same applies to a "horizontal direction". The "horizontal direction" refers not only to a perfect horizontal direction but also to a horizontal direction in the sense of including an error that is generally acceptable in the technical field to which the technology of the present disclosure belongs and that does not contradict the concept of the technology of the present disclosure.

Figure 1:
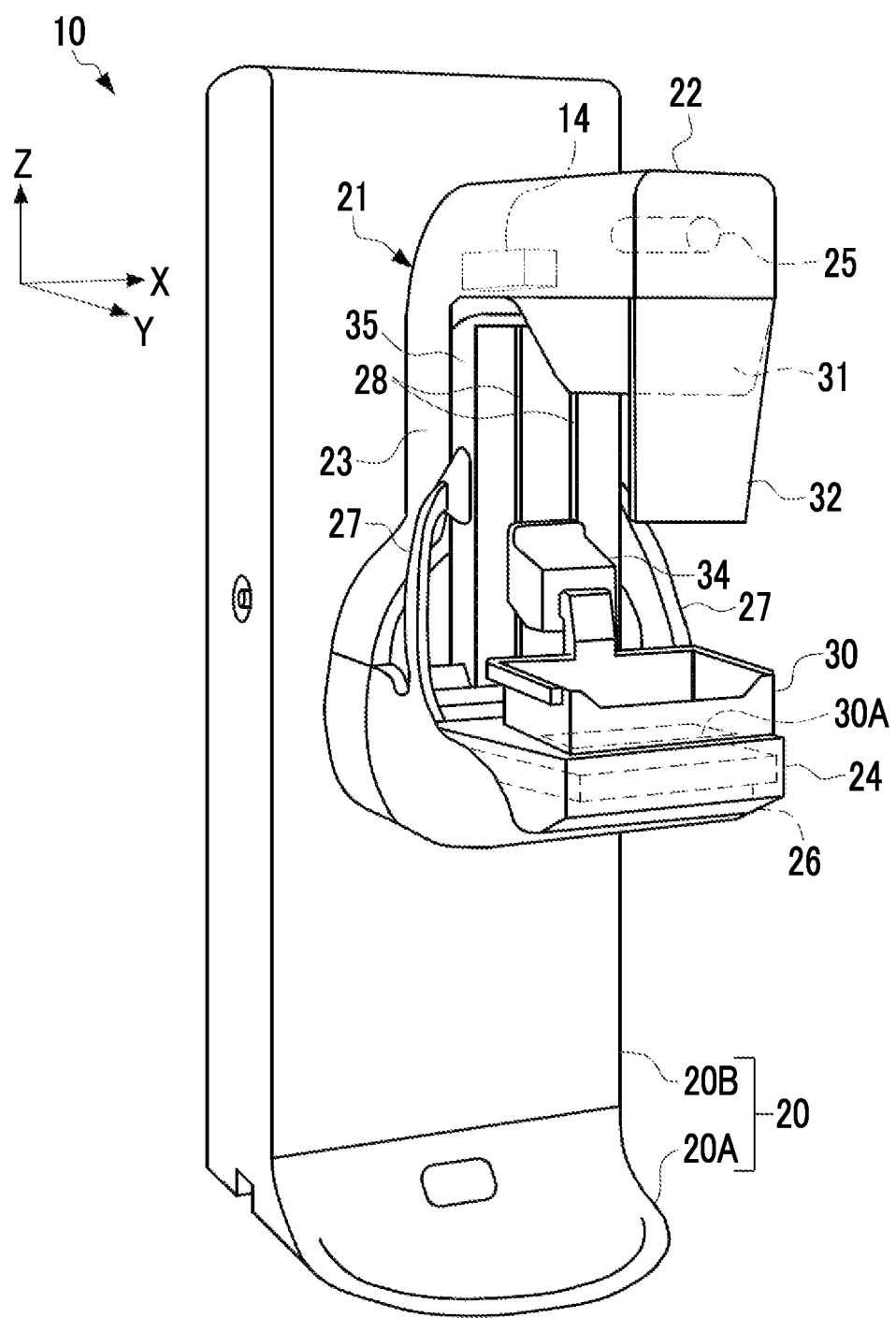
FIG. 1 is an external perspective view showing an example of a configuration of a mammography apparatus.
Figure 2:
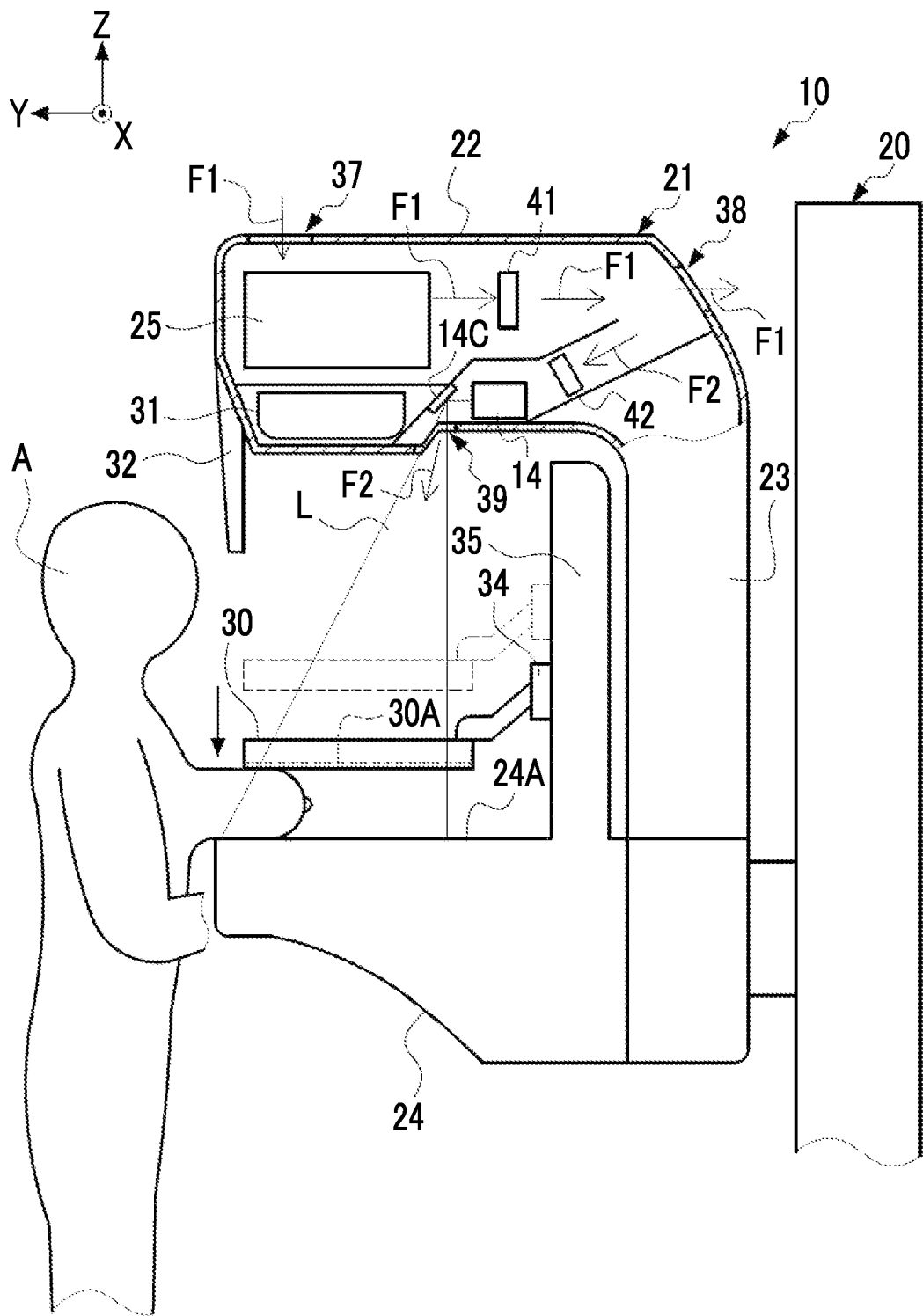
FIG. 2 is an external side view showing an example of the configuration of the mammography apparatus.

As shown in FIGS. 1 and 2, the mammography apparatus 10 according to a first embodiment is a radiography apparatus that irradiates a breast M of the subject A to be examined with radiation and captures a radiographic image of the breast M. The radiation is X-rays as an example, but y-rays may also be used. The subject A is located on the front side with respect to the mammography apparatus 10. The mammography apparatus 10 is an example of a "mammography apparatus" according to the technology of the present disclosure.

The mammography apparatus 10 is connected to a console (not shown). The console has a setting function of setting the mammography apparatus 10 in accordance with an imaging order and a function of acquiring a radiographic image captured by the mammography apparatus 10 and displaying the acquired radiographic image. The console is communicably connected to an image database server (not shown) via a network (not shown) such as a local area network (LAN).

The mammography apparatus 10 includes a stand 20 and an arm 21. The stand 20 includes a pedestal 20A that is provided on a floor of a radiography room and a support column 20B that extends from the pedestal 20A in a height direction. The arm 21 has a substantially C-shape as viewed from the left side and is connected to the support column 20B. Since the arm 21 is movable in a height direction with respect to the support column 20B, a height of the arm 21 can be adjusted according to a height of the subject A. The arm 21 is rotatable about a rotation axis perpendicular to the support column 20B. The stand 20 is an example of a "stand" according to the technology of the present disclosure. The arm 21 is an example of an "arm" according to the technology of the present disclosure.

The arm 21 is composed of a radiation source accommodation portion 22, a main body portion 23, and an imaging table 24. A radiation source 25 is accommodated in the radiation source accommodation portion 22. The radiation source accommodation portion 22 has, for example, a housing structure having a longitudinal direction in the horizontal direction (that is, a direction along the Y direction shown in FIG. 2). The breast M of the subject A is placed on the imaging table 24. A radiation detector 26 is accommodated in the imaging table 24. The main body portion 23 integrally connects the radiation source accommodation portion 22 and the imaging table 24. The main body portion 23 holds the radiation source accommodation portion 22 and the imaging table 24 at positions facing each other. Handrails 27 for the subject A to hold are provided on both sides of the main body portion 23.

The radiation source 25 emits radiation toward the breast M placed on the imaging table 24. The radiation source 25 is an example of a "radiation source" according to the technology of the present disclosure. The radiation emitted from the radiation source 25 is transmitted through the compression plate 30 and then is incident on the breast M. The radiation detector 26 detects the radiation transmitted through the breast M and outputs a radiographic image. The radiation detector 26 is referred to as a flat panel detector (FPD). The radiation detector 26 may be an indirect conversion type that includes a scintillator converting the radiation into visible light and converts the visible light emitted from the scintillator into an electric signal or a direct conversion type that directly converts the radiation into an electric signal.

An irradiation field limiter 31 is provided between the radiation source accommodation portion 22 and the imaging table 24. The irradiation field limiter 31 is also referred to as a collimator and defines an irradiation field of the radiation to the imaging table 24.

A face guard 32 is attached to the radiation source accommodation portion 22. The face guard 32 is formed of or coated with a material not transmitting the radiation and protects a face of the subject A from the radiation.

The compression plate 30 is provided between the imaging table 24 and the irradiation field limiter 31 to sandwich the breast M with the imaging table 24 and compress the breast M. The compression plate 30 is formed of a material that transmits the radiation. The compression plate 30 is disposed at a position facing the imaging table 24. In the present embodiment, the compression plate 30 has a box shape in which an upper surface side is open. The compression plate 30 may have other shapes such as a flat plate shape.

A drive mechanism 35 movably supports the compression plate 30 between the radiation source 25 and the imaging table 24. Further, a movable portion 34 is disposed between the compression plate 30 and the drive mechanism 35. The movable portion 34 is slidably held by a rail 28 provided in the drive mechanism 35. The rail 28 extends in an up-down direction.

The compression plate 30 is attached to the movable portion 34. The movable portion 34 moves in the up-down direction together with the compression plate 30 by the drive mechanism 35 described later. The up-down direction is functionally a direction in which the compression plate 30 moves toward the imaging table 24 (that is, the downward direction) and a direction in which the compression plate 30 moves away from the imaging table 24 (that is, the upward direction). As described above, the compression plate 30 is configured to be movable in such a manner that a distance from the imaging table 24 is changed.

A projector 14 is accommodated in the radiation source accommodation portion 22. The projector 14 emits projection light L through an emission port 39. The projector 14 projects an image toward an imaging surface 24A of the imaging table 24. Here, the imaging surface 24A is a surface facing the radiation source 25 on the imaging table 24. In addition, the projector 14 projects an image toward a surface facing the radiation source 25 on the compression plate 30. Since the compression plate 30 of the present embodiment has a box shape, a bottom surface 30A of the box shape is a surface facing the radiation source 25. The projector 14 projects an image toward the bottom surface 30A of the compression plate 30. The projector 14 is an example of a "projector" according to the technology of the present disclosure.

The radiation source accommodation portion 22 accommodates a radiation source cooling fan 41 and a projector cooling fan 42. The radiation source cooling fan 41 is a fan for cooling the radiation source 25. The radiation source cooling fan 41 sucks air from the outside of the arm 21 and further exhausts the air to the outside of the arm 21. Accordingly, an airflow F1 of the air passing through the radiation source is generated in the arm 21. The projector cooling fan 42 is a fan for cooling the projector. The projector cooling fan 42 sucks a part of the air directed from the radiation source cooling fan 41 to the outside and blows the sucked air toward the projector 14. As a result, an airflow F2 of the air passing through the projector 14 is generated in the arm 21. The radiation source cooling fan 41 is an example of a "first cooling fan" according to the technology of the present disclosure, and the projector cooling fan 42 is an example of a "second cooling fan" according to the technology of the present disclosure.

Figure 3:
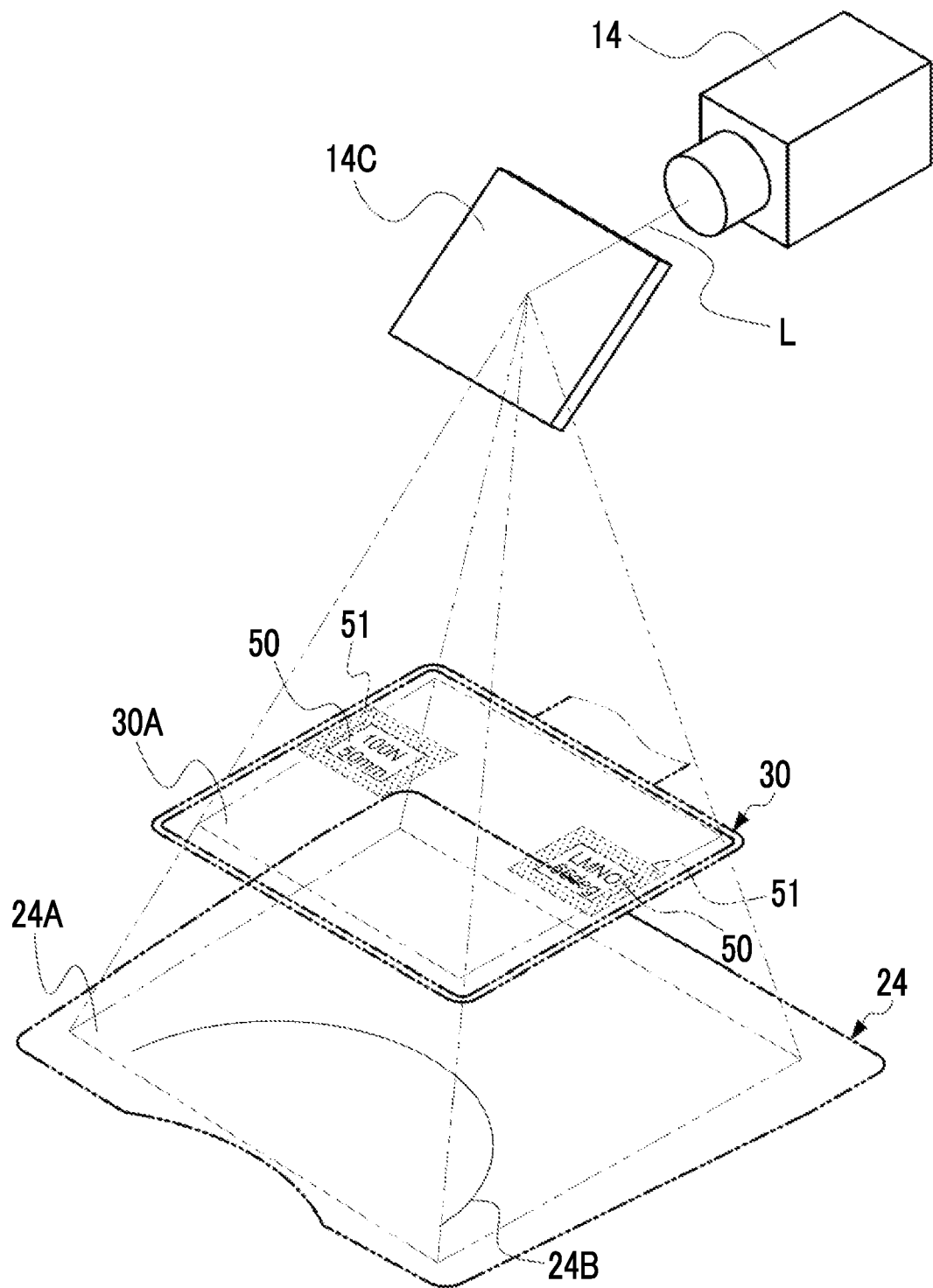
FIG. 3 is a schematic view showing an example of projection of an image in the mammography apparatus.

As shown in FIG. 3, in the mammography apparatus 10, the projection light L is emitted from the projector 14 so that imaging condition information 50 is projected onto the compression plate 30, and a skin line 24B is projected onto the imaging surface 24A.

Imaging conditions indicated by the imaging condition information 50 include a current compression pressure, compression thickness, or type of imaging technique for the breast M. Examples of the imaging technique include cranio-caudal (CC) imaging and medio-lateral (MLO) imaging. The imaging condition information 50 is an example of "information" according to the technology of the present disclosure.

In the bottom surface 30A of the compression plate 30, a region 51 onto which the imaging condition information 50 is projected is subjected to a process of suppressing transmission of light (for example, blasting process). As a result, the projection light L representing the imaging condition information 50 is less likely to transmit through the compression plate 30, and an amount of reflected light on the compression plate 30 increases, so that the imaging condition information 50 is clearly visible.

Portions of the compression plate 30 other than the region 51 are made of a material transparent to the projection light L. Therefore, the projection light L transmitted through the compression plate 30 is projected onto the imaging surface 24A. A skin line 24B indicating a contour of the breast M, which is an index for placing the breast M, is projected onto the imaging surface 24A. The skin line 24B is an example of "information" according to the technology of the present disclosure. In addition, instead of the skin line 24B or together with the skin line 24B, a mark indicating a position of a papilla of the breast M (for example, a mark of a cross having an intersection at the position of the papilla) may be projected onto the imaging surface 24A.

The breast M of the subject A is positioned on the imaging surface 24A of the imaging table 24 by a user. The breast M is compressed by the compression plate 30 in a state in which the breast M is positioned.

Here, an example of a form in which the imaging condition information 50 is projected onto the compression plate 30, and the skin line 24B is displayed on the imaging surface 24A has been described, but the technology of the present disclosure is not limited thereto. For example, an aspect in which the imaging condition information 50 and the skin line 24B are displayed on the compression plate 30 may be employed.

Figure 4:
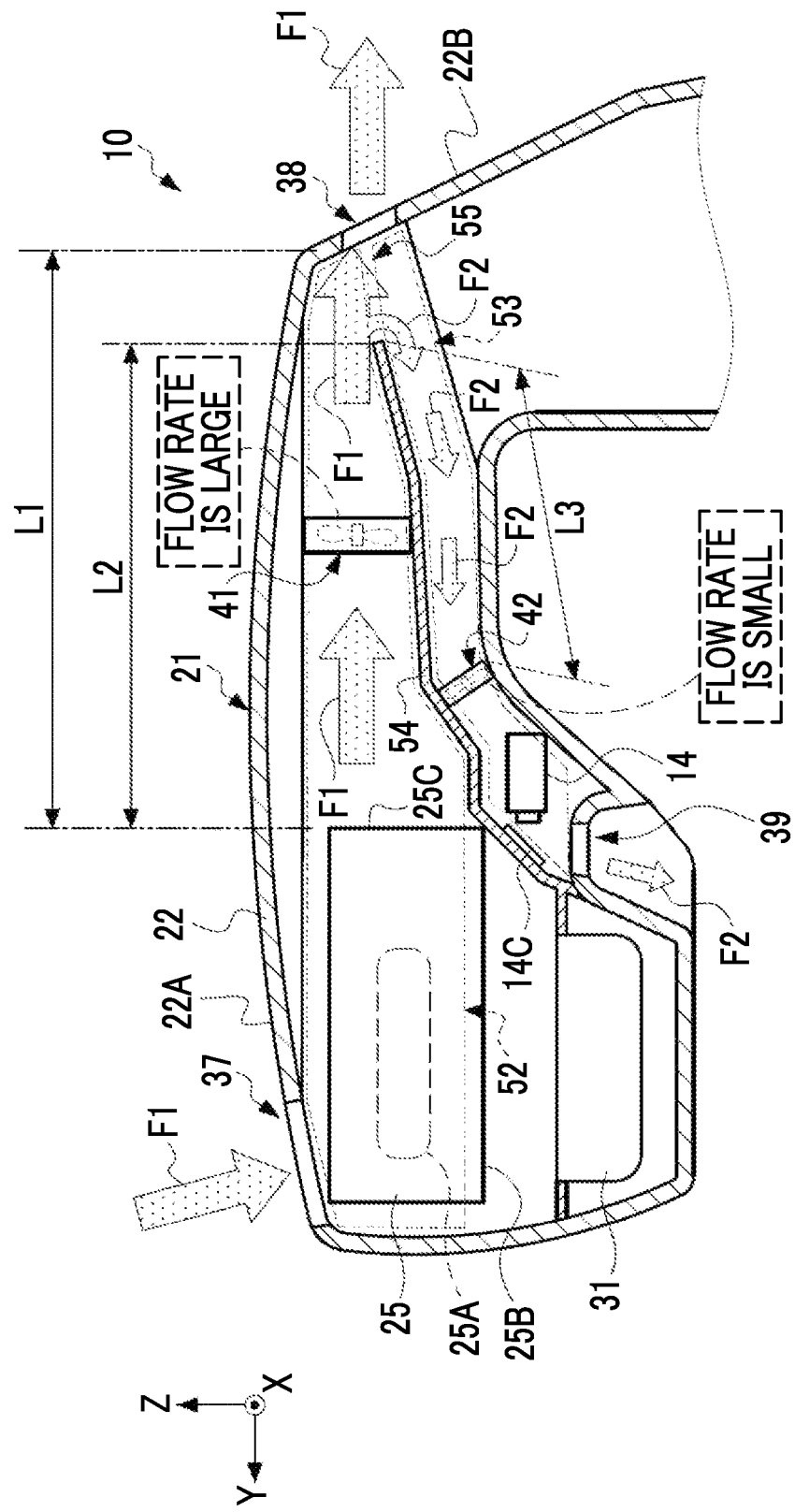
FIG. 4 is a side view showing an example of a flow of air in the mammography apparatus.

As shown in FIG. 4, the radiation source cooling fan 41 is disposed on the stand 20 side (that is, the rear side) with respect to the radiation source 25 in the horizontal direction (a direction along the Y direction shown in FIG. 4). The radiation source cooling fan 41 sucks the air from the front side of the radiation source accommodation portion 22 and exhausts the air to the rear side of the radiation source accommodation portion 22. Specifically, an air supply port 37 is provided on the front side of a top wall 22A of the radiation source accommodation portion 22. Further, an exhaust port 38 is provided on the upper side of a rear wall 22B of the radiation source accommodation portion 22. The radiation source cooling fan 41 sucks outside air from the air supply port 37 and exhausts the air toward the exhaust port 38. The exhaust port 38 is an example of a "first exhaust port" according to the technology of the present disclosure.

The radiation source cooling fan 41 generates the airflow F1. The airflow F1 is a flow of air that enters into the radiation source accommodation portion 22 from the air supply port 37, passes through an upper flow path 52 in the radiation source accommodation portion 22, and is discharged to the outside from the exhaust port 38. The radiation source 25 is provided below the air supply port 37. As the airflow F1 hits the radiation source 25, heat of the radiation source 25 is transferred to the airflow F1 and the radiation source 25 is cooled. The airflow F1 that has cooled the radiation source 25 is discharged toward the exhaust port 38 through the radiation source cooling fan 41.

The projector cooling fan 42 is disposed between the exhaust port 38 and the projector 14 in the horizontal direction. The projector cooling fan 42 sucks a part of the airflow F1 discharged from the radiation source cooling fan 41 and directed to the exhaust port 38, and blows the sucked airflow toward the projector 14. The airflow F2 is generated by the projector cooling fan 42. The airflow F2 is a flow of air in which a part of the airflow F1 is directed to the emission port 39 of the projector 14. As the airflow F2 hits the projector 14, heat of the projector 14 is transferred to the airflow F2 and the projector 14 is cooled. Here, in general, a temperature (for example, about 70° C.) of heat generated in the projector 14 mounted on the mammography apparatus 10 is higher than a temperature (for example, about 40° C.) of heat generated in the radiation source 25. Therefore, even the air after cooling the radiation source 25 can cool the projector 14 because the air has a temperature lower than the temperature of the heat generated in the projector 14.

The airflow F2 that has cooled the projector 14 is discharged from the emission port 39 of the projector 14. In other words, the emission port 39 also serves as an opening through which the airflow F2 is discharged. The emission port 39 is an example of an "emission port" and a "second exhaust port" according to the technology of the present disclosure.

A flow rate of the projector cooling fan 42 is smaller than a flow rate of the radiation source cooling fan 41. Here, the flow rate refers to a volume of air passing through the fan per unit time. In general, a size of the projector 14 mounted on the mammography apparatus 10 is smaller than a size of the radiation source 25. As described above, the temperature of the radiation source 25 is lower than the temperature of the projector 14. However, the size of the radiation source 25 is larger than the size of the projector 14. Therefore, it is necessary to increase the flow rate of the radiation source cooling fan 41, and the flow rate of the projector cooling fan 42 becomes relatively small. Referring to FIG. 4, a flow rate of the airflow F2 is smaller than a flow rate of the airflow F1.

The upper flow path 52 and a lower flow path 53 are formed in the radiation source accommodation portion 22. The upper flow path 52 and the lower flow path 53 are formed by dividing the inside of the radiation source accommodation portion 22 into upper and lower parts in the vertical direction by a partition plate 54. The upper flow path 52 is a flow path formed on the upper side of the partition plate 54 in the radiation source accommodation portion 22. The radiation source cooling fan 41 is disposed in the upper flow path 52. The upper flow path 52 is a flow path directed at least from the radiation source cooling fan 41 to the exhaust port 38. In an example shown in FIG. 4, the upper flow path 52 guides the airflow F1 from the air supply port 37 to the exhaust port 38. That is, the upper flow path 52 causes the airflow F1 to propagate in a predetermined path in the radiation source accommodation portion 22, and prevents the airflow F1 from flowing into the other airflow F2. The upper flow path 52 is an example of a "first flow path" according to the technology of the present disclosure, and the lower flow path 53 is an example of a "second flow path" according to the technology of the present disclosure. Further, the partition plate 54 is an example of a "partition" according to the technology of the present disclosure.

The lower flow path 53 is a flow path formed on the lower side of the partition plate 54 in the radiation source accommodation portion 22. The lower flow path 53 is a flow path directed from a branch portion 55 to the emission port 39. The branch portion 55 is a region where the upper flow path 52 branches between the radiation source cooling fan 41 and the exhaust port 38. In other words, the upper flow path 52 and the lower flow path 53 are partitioned by the partition plate 54 except for the branch portion 55. The projector 14 and the projector cooling fan 42 are disposed in the lower flow path 53. The lower flow path 53 guides the airflow F2 from the branch portion 55 to the emission port 39. That is, the lower flow path 53 causes the airflow F2 to propagate in a predetermined path in the radiation source accommodation portion 22 and prevents the airflow F2 from flowing into the other airflow F1. The branch portion 55 is an example of a "branch portion" according to the technology of the present disclosure.

In a case where the upper flow path 52 and the lower flow path 53 are viewed from the side of the mammography apparatus 10 (that is, in case of being viewed from the X direction shown in FIG. 4), the upper flow path 52 and the lower flow path 53 form a V-shape (that is, a shape of ">") with the branch portion 55 as an apex. That is, the lower flow path 53 is branched from the upper flow path 52 so as to be folded back at the branch portion 55. Here, the projector 14 is disposed on the radiation source 25 side (that is, the front side) with respect to the radiation source cooling fan 41 and the projector cooling fan 42. Thus, a distance from the radiation source cooling fan 41 to the projector 14 is ensured.

For example, the radiation source 25 includes a bulb 25A that generates radiation and a container 25B that accommodates the bulb 25A. The container 25B is an insulating container that accommodates the bulb 25A in a state in which a periphery of the bulb 25A is filled with insulating oil. In the container 25B, a distance from an end surface 25C (that is, a rear end surface 25C) of the container 25B on the radiation source cooling fan 41 side to the exhaust port 38 is defined as L1. Here, the distance L1 is the shortest distance along the upper flow path 52 from the rear end surface 25C to the exhaust port 38 in a case where the upper flow path 52 is viewed sideways. On the other hand, a distance from the rear end surface 25C to the branch portion 55 is defined as L2. Further, a distance from the branch portion 55 to the projector cooling fan 42 is defined as L3. The distance L2 is the shortest distance along the upper flow path 52 from the rear end surface 25C to the branch portion 55 in a case where the upper flow path 52 is viewed sideways. In addition, the distance L3 is the shortest distance along the lower flow path 53 from the branch portion 55 to the projector cooling fan 42 in a case where the lower flow path 53 is viewed sideways.

In this case, a sum of the distances L2 and the distance L3 is longer than the distance L1 (that is, L2+L3>L1). In this way, a distance from the rear end surface 25C of the radiation source 25 to the projector cooling fan 42 via the branch portion 55 is set to be longer than the distance from the rear end surface 25C to the exhaust port. Therefore, the distance from the radiation source cooling fan 41 to the projector 14 is ensured.

Figure 5:
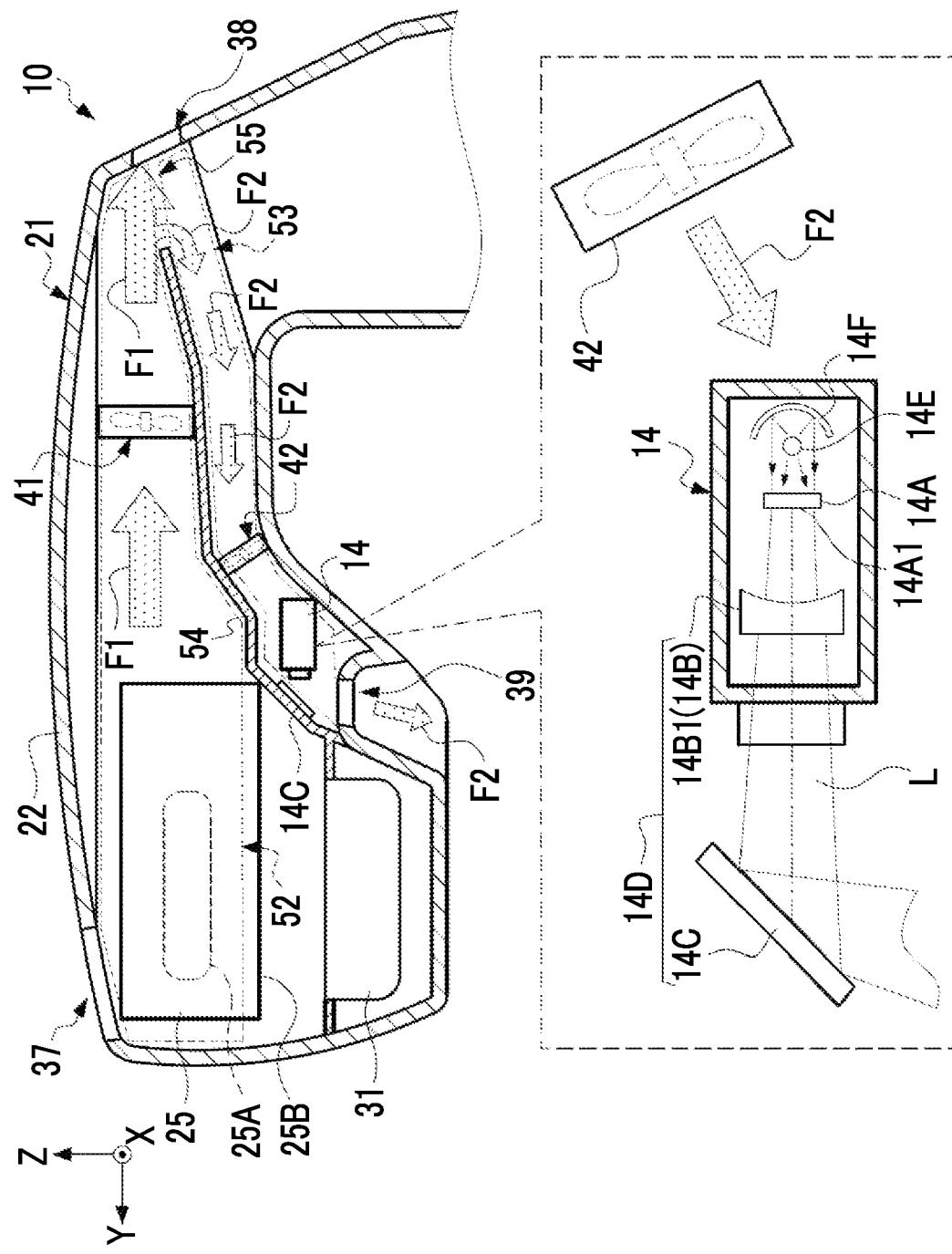
FIG. 5 is a side view showing an example of the flow of the air in the mammography apparatus.

As shown in FIG. 5, the projector 14 includes a display 14A, a projection optical system 14D, and a light source 14E. The display 14A projects an image displayed on an image display surface 14A1. Examples of the display 14A include a liquid crystal display (LCD). As is well known, the LCD comprises a plurality of liquid crystal cells corresponding to a plurality of pixels, and changes a transmission state of light from the light source 14E for each liquid crystal cell to perform optical modulation according to an image to be projected. In a case where the display 14A is the LCD, an arrangement surface on which the plurality of liquid crystal cells are two-dimensionally arranged corresponds to the image display surface 14A1. The projection optical system 14D includes a built-in optical system 14B and a mirror 14C. The built-in optical system 14B is an optical system including a lens 14B1. In addition, the mirror 14C reflects the projection light L emitted from the built-in optical system 14B to emit the projection light L to the compression plate 30 and the imaging surface 24A. The light source 14E emits the projection light L toward the display 14A. Further, a reflecting plate 14F is provided on a side of the light source 14E opposite to the display 14A, and the reflecting plate 14F reflects a part of the projection light L toward the display 14A. Accordingly, it is possible to increase a light quantity of the projection light L directed to the display 14A. The light source 14E is an example of a "light source" according to the technology of the present disclosure.

Although an example of a form in which the LCD is used as the display 14A has been described here, this is only an example. For example, a digital micromirror device (DMD) may be used as the display 14A. As is well known, the DMD comprises a plurality of micromirrors corresponding to a plurality of pixels. As an example, by changing an angle of each micromirror, a reflection direction of the light from the light source 14E is changed between on-light that is incident on the projection optical system 14D and off-light that is not incident on the projection optical system 14D. Then, a light quantity for each pixel is adjusted according to the duration of the on-light.

In the projector 14, the light source 14E is disposed on the projector cooling fan 42 side with respect to the emission port 39. In other words, the airflow F2 discharged from the projector cooling fan 42 is directed to the light source 14E. A main heat source in the projector 14 is the light source 14E. In a case where the airflow F2 after being discharged from the projector cooling fan 42 hits a portion of the projector 14 on the light source 14E side, the heat of the projector 14 (for example, heat generated from the light source 14E) is transferred to the airflow F2.

As described above, in the mammography apparatus 10 according to the present embodiment, the radiation source cooling fan 41 that sucks the air from the outside and discharges the air that has cooled the radiation source 25 from the exhaust port 38 provided in the rear wall 22B of the radiation source accommodation portion 22 is provided in the radiation source accommodation portion 22. In addition, the projector cooling fan 42 that sucks a part of the air directed from the radiation source cooling fan 41 to the exhaust port 38 and blows the sucked air toward the projector 14 to cool the projector 14 is provided in the radiation source accommodation portion 22. Further, the flow rate of the projector cooling fan 42 is set to be smaller than that of the radiation source cooling fan 41. Then, the air that has cooled the projector 14 is discharged from the emission port 39. Thus, a cooling efficiency of the projector 14 is improved.

Figure 6:
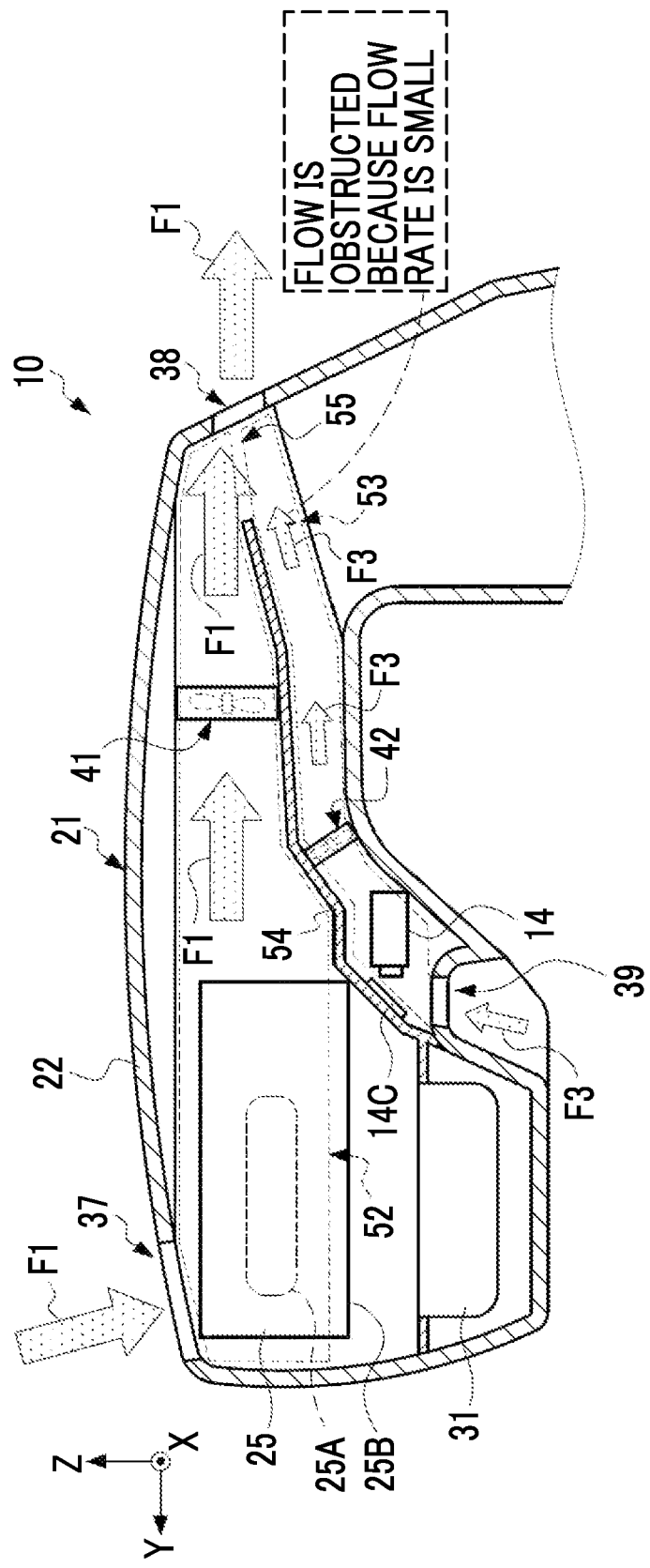
FIG. 6 is a side view showing an example of an internal structure of a mammography apparatus according to a comparative example.

For example, as shown in FIG. 6 as a comparative example, in a case where a cooling fan that sucks air from the outside and discharges the air that has cooled the projector 14 from the exhaust port 38 in the same manner as the radiation source cooling fan 41 is used as the projector cooling fan 42, there is the following problem. That is, in a case where the flow rate of the projector cooling fan 42 is smaller than the flow rate of the radiation source cooling fan 41, the flow of the air directed from the projector cooling fan 42 to the exhaust port 38 (that is, the airflow F3) is lost to momentum of the air directed from the radiation source cooling fan 41 to the exhaust port 38. As a result, the airflow F3 that cools the projector 14 does not flow smoothly, which causes a problem in that the cooling efficiency of the projector 14 is decreased.

In the present configuration, the projector cooling fan 42 sucks a part of the air directed from the radiation source cooling fan 41 toward the exhaust port 38 and blows the sucked air toward the projector 14. Then, the air that has cooled the projector 14 is discharged from the emission port 39 which is different from the exhaust port 38. Therefore, since the projector cooling fan 42 does not allow the air to flow toward the same exhaust port 38 as that of the radiation source cooling fan 41, even in a case where the flow rate of the projector cooling fan 42 is smaller than the flow rate of the radiation source cooling fan 41, the air that cools the projector 14 can flow smoothly. Thus, a cooling efficiency of the projector 14 is improved.

Further, for example, in the present configuration, the airflow F1 discharged from the radiation source cooling fan 41 is discharged from the exhaust port 38 as well as a part thereof is discharged from the emission port 39 as the airflow F2. For this reason, as compared to the comparative example shown in FIG. 6, exhausting by the radiation source cooling fan 41 is also efficiently performed, so that a cooling efficiency of the radiation source 25 is also improved.

In the comparative example shown in FIG. 6, for example, it is also conceivable to exhaust the air from the exhaust port 38 by making the flow rate of the projector cooling fan 42 larger than that of the radiation source cooling fan 41. However, in this case, a power consumption in the projector cooling fan 42 increases, and a noise caused by the air blowing becomes a problem. According to the present configuration, an effect of improving the cooling efficiency of the projector 14 can be expected while solving the problem of increasing the size of the projector cooling fan 42.

In addition, in the mammography apparatus 10 according to the present embodiment, the radiation source accommodation portion 22 is provided with the upper flow path 52 and the lower flow path 53. The radiation source cooling fan 41 is disposed in the upper flow path 52. The projector cooling fan 42 and the projector 14 are disposed in the lower flow path 53, and the lower flow path 53 is a flow path directed from the branch portion 55 to the emission port 39. In a region other than the branch portion 55, the partition plate 54 is provided between the upper flow path 52 and the lower flow path 53. Since the inflow of air from the upper flow path 52 to the lower flow path 53 from portions other than the branch portion 55 is suppressed, turbulence in the flow of the air that cools the projector 14 can be suppressed. Thus, a cooling efficiency of the projector 14 is improved.

In addition, in the mammography apparatus 10 according to the present embodiment, in a case where the distance L1 is from the rear end surface 25C to the exhaust port 38, the distance L2 is from the rear end surface 25C to the branch portion 55, and the distance L3 is from the branch portion 55 to the projector cooling fan 42, the sum of the distance L2 and the distance L3 is longer than the distance L1. Accordingly, as compared to a case where the sum of the distance L2 and the distance L3 is shorter than the distance L1, a cooling period of the airflow F2 that is sucked by the projector cooling fan 42 and blown to the projector 14 becomes longer. Therefore, a temperature of the airflow F2 is sufficiently lowered, and the cooling efficiency of the projector 14 by the projector cooling fan 42 is improved.

Further, in the mammography apparatus 10 according to the present embodiment, the light source 14E of the projector 14 is disposed on the projector cooling fan 42 side with respect to the exhaust port 38. In the projector 14, the light source 14E is a main heat source. The light source 14E of the projector 14 is disposed on the projector cooling fan 42 side with respect to the emission port 39. In other words, the projector cooling fan 42 blows the air toward the light source 14E of the projector 14. As a result, a flow rate of the air blown to the light source 14E of the projector 14 is larger than that of a case where the light source 14E of the projector 14 is disposed on the emission port 39 side with respect to the projector 14, so that the cooling efficiency of the projector 14 is improved.

For example, in the comparative example shown in FIG. 6, the projector cooling fan 42 sucks the air from the emission port 39 and exhausts the air toward the exhaust port 38. Further, the projector 14 is disposed between the emission port 39 and the exhaust port 38 in the lower flow path 53. Therefore, the projector cooling fan 42 sucks the air from the projector 14 side and discharges the air toward the exhaust port 38. That is, in the comparative example shown in FIG. 6, the projector cooling fan 42 does not blow the air toward a heat source of the projector 14. In this case, the cooling efficiency is decreased as compared to a case where the projector 14 is disposed on an exhaust side of the projector cooling fan 42 and is cooled. In the present configuration, the projector cooling fan 42 blows the air toward the heat source of the projector 14, so that the projector 14 can be cooled more efficiently.

Further, in the present configuration, as described above, since the projector 14 is cooled by using the air that has cooled the radiation source 25, it is required to improve the cooling efficiency in the cooling of the projector 14. Therefore, in the present configuration, by disposing the light source 14E of the projector 14 on the projector cooling fan 42 side with respect to the exhaust port 38, the flow rate of the air blown to the light source 14E of the projector 14 increases, and the cooling efficiency of the projector 14 is improved.

Further, in the mammography apparatus 10 according to the present embodiment, the emission port 39 through which the projection light L is emitted from the projector 14 also serves as an opening for exhausting the air that has cooled the projector 14. As a result, the air flowing from the emission port 39 toward the projector 14 is suppressed, so that adhesion of dust or the like to the projection optical system 14D of the projector 14 is suppressed.

Further, in the mammography apparatus 10 according to the present embodiment, the projector 14 is disposed on the radiation source 25 side with respect to the radiation source cooling fan 41 and the projector cooling fan 42, and in a case where the upper flow path 52 and the lower flow path 53 are viewed as a whole, the upper flow path 52 and the lower flow path 53 form a V-shape with the branch portion 55 as an apex. Accordingly, since two flow paths of the upper flow path 52 and the lower flow path 53 can be partitioned by one partition plate 54, it is easy to simplify the configuration as compared to a shape having a plurality of folded portions. In addition, by forming the V-shape, an effect that a thickness of the radiation source accommodation portion 22 in the height direction can be suppressed can also be expected as compared to a case of, for example, an L-shape.

The above embodiment has been described with an example of a form in which the air supply port 37 is provided on the front side of the top wall 22A of the radiation source accommodation portion 22, but the technology of the present disclosure is not limited thereto. For example, the air supply port 37 may be provided on a front wall of the radiation source accommodation portion 22. In addition, the above embodiment has been described with an example of a form in which the exhaust port 38 is provided on the rear wall 22B of the radiation source accommodation portion 22, but the technology of the present disclosure is not limited thereto. For example, the exhaust port 38 may be provided on the rear side of the top wall 22A of the radiation source accommodation portion 22.

The above embodiment has been described with an example of a form in which the airflow F2 is discharged from the emission port 39, but the technology of the present disclosure is not limited thereto. For example, the airflow F2 may be discharged from an opening provided on a lower surface of the radiation source accommodation portion 22 separately from the emission port 39.

In addition, the above embodiment has been described with an example of a form in which the upper flow path 52 and the lower flow path 53 are formed by the partition plate 54, but the technology of the present disclosure is not limited thereto. For example, the upper flow path 52 and the lower flow path 53 may be formed by a tubular member provided in the radiation source accommodation portion 22.

The above-described contents and illustrated contents are detailed descriptions of parts related to the technology of the present disclosure, and are merely examples of the technology of the present disclosure. For example, the above descriptions related to configurations, functions, operations, and advantages effects are descriptions related to examples of configurations, functions, operations, and advantages effects of the parts related to the technology of the present disclosure. Therefore, it is needless to say that unnecessary parts may be deleted, or new elements may be added or replaced with respect to the above-described contents and illustrated contents within a scope not departing from the spirit of the technology of the present disclosure. In order to avoid complication and easily understand the parts according to the technology of the present disclosure, in the above-described contents and illustrated contents, common technical knowledge and the like that do not need to be described to implement the technology of the present disclosure are not described.

All documents, patent applications, and technical standards described in the present specification are incorporated in the present specification by reference to the same extent as in a case where each document, patent application, and technical standard are specifically and individually noted to be incorporated by reference.

Furthermore, the following appendices will be disclosed in relation to the above-described embodiment.

APPENDIX 1

A mammography apparatus comprising: an arm that accommodates a radiation source emitting radiation toward a breast and is supported by a stand; a first cooling fan that is disposed on a stand side with respect to the radiation source in the arm, sucks air from an outside of the arm, and discharges air that has cooled the radiation source from a first exhaust port provided on the stand side with respect to the radiation source; a projector that is disposed in the arm and projects information; a second cooling fan that is disposed between the projector and the first exhaust port in the arm, sucks a part of air directed from the first cooling fan to the first exhaust port, blows the sucked air toward the projector to cool the projector, and has a flow rate smaller than that of the first cooling fan; and a second exhaust port that is provided separately from the first exhaust port and through which air that has cooled the projector is discharged.

APPENDIX 2

The mammography apparatus according to appendix 1, further comprising: a first flow path in which the first cooling fan is disposed and that is directed from the first cooling fan to the first exhaust port; and a second flow path that is directed from a branch portion branching from the first flow path to the second exhaust port between the first cooling fan and the first exhaust port and in which the second cooling fan and the projector are disposed, in which a partition is provided between the first flow path and the second flow path except for the branch portion.

APPENDIX 3

The mammography apparatus according to appendix 2, in which a first distance from an end surface of the radiation source on a first cooling fan side to the second cooling fan via the branch portion is longer than a second distance from the end surface to the first exhaust port.

APPENDIX 4

The mammography apparatus according to any one of appendices 1 to 3, in which a light source of the projector is disposed on a second cooling fan side with respect to the second exhaust port.

APPENDIX 5

The mammography apparatus according to any one of appendices 1 to 4, in which an emission port through which projection light is emitted from the projector also serves as the second exhaust port.

APPENDIX 6

The mammography apparatus according to appendix 2 or 3, in which the projector is disposed on a radiation source side with respect to the first cooling fan and the second cooling fan, and in a case where the first flow path and the second flow path are viewed as a whole, the first flow path and the second flow path form a V-shape with the branch portion as an apex.

What is claimed is:

1. A mammography apparatus comprising:
   an arm that accommodates a radiation source emitting radiation toward a breast and is supported by a stand;
   a first cooling fan that is disposed on a stand side with respect to the radiation source in the arm, sucks air from an outside of the arm, and discharges air that has cooled the radiation source from a first exhaust port provided on the stand side with respect to the radiation source;
   a projector that is disposed in the arm and projects information;
   a second cooling fan that is disposed between the projector and the first exhaust port in the arm, sucks a part of air directed from the first cooling fan to the first exhaust port, blows the sucked air toward the projector to cool the projector, and has a flow rate smaller than that of the first cooling fan; and
   a second exhaust port that is provided separately from the first exhaust port and through which air that has cooled the projector is discharged.

2. The mammography apparatus according to claim 1, further comprising:
   a first flow path in which the first cooling fan is disposed and that is directed from the first cooling fan to the first exhaust port; and
   a second flow path that is directed from a branch portion branching from the first flow path to the second exhaust port between the first cooling fan and the first exhaust port and in which the second cooling fan and the projector are disposed,
   wherein a partition is provided between the first flow path and the second flow path except for the branch portion.

3. The mammography apparatus according to claim 2, wherein a first distance from an end surface of the radiation source on a first cooling fan side to the second cooling fan via the branch portion is longer than a second distance from the end surface to the first exhaust port.

4. The mammography apparatus according to claim 2, wherein the projector is disposed on a radiation source side with respect to the first cooling fan and the second cooling fan, and
   in a case where the first flow path and the second flow path are viewed as a whole, the first flow path and the second flow path form a V-shape with the branch portion as an apex.

5. The mammography apparatus according to claim 1, wherein a light source of the projector is disposed on a second cooling fan side with respect to the second exhaust port.

6. The mammography apparatus according to claim 1, wherein an emission port through which projection light is emitted from the projector also serves as the second exhaust port.

* * * * *